US012343100B2

(12) United States Patent
Cau et al.

(10) Patent No.: US 12,343,100 B2
(45) Date of Patent: Jul. 1, 2025

(54) SURGICAL ROBOTIC SYSTEM WITH ADJUSTABLE ANGLE OF APPROACH

(71) Applicant: MICROSURE B.V., Son (NL)

(72) Inventors: Raimondo Cau, Son (NL); Tom Konert, Son (NL)

(73) Assignee: MICROSURE B.V., Son (NL)

( * ) Notice: Subject to any disclaimer, the term of this patent is extended or adjusted under 35 U.S.C. 154(b) by 326 days.

(21) Appl. No.: 17/997,508

(22) PCT Filed: Mar. 29, 2021

(86) PCT No.: PCT/EP2021/058213
§ 371 (c)(1),
(2) Date: Oct. 28, 2022

(87) PCT Pub. No.: WO2021/219311
PCT Pub. Date: Nov. 4, 2021

(65) Prior Publication Data
US 2023/0172678 A1 Jun. 8, 2023

(30) Foreign Application Priority Data
Apr. 29, 2020 (EP) ...................... 20172047

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/71* (2016.02); *A61B 90/06* (2016.02);
(Continued)

(58) Field of Classification Search
CPC ......... A61B 34/37; A61B 34/71; A61B 90/06; A61B 2034/2059; A61B 2034/305; A61B 2034/742; A61B 2090/065
See application file for complete search history.

(56) References Cited

U.S. PATENT DOCUMENTS 6,659,939 B2 * 12/2003 Moll ...................... A61B 34/35
600/102
2019/0125455 A1 * 5/2019 Shelton, IV ........... A61B 5/061
(Continued)

FOREIGN PATENT DOCUMENTS

WO 2006124390 A1 11/2006
WO 2006124390 A3 11/2006
(Continued)

OTHER PUBLICATIONS

ISA European Patent Office, International Search Report and Written Opinion Issued in Application No. PCT/EP2021/058213, Jun. 9, 2021, WIPO, 14 pages.

*Primary Examiner* — Jason Holloway
*Assistant Examiner* — Christopher A Buksa
(74) *Attorney, Agent, or Firm* — McCoy Russell LLP

(57) ABSTRACT

A surgical robotic system is provided including a suspension structure, a manipulator arm for holding a surgical instrument, one or more actuators to adjust a pose of the manipulator arm, and a control system configured to establish a master-slave coupling between a user input device as a master device and the manipulator arm as a slave device. The manipulator may be manually reconfigurable from a first configuration in which the manipulator arm assumes a first pose to a second configuration in which the manipulator arm assumes a second pose which is mirrored with respect to the first pose about a mirroring plane which runs through a tip of the surgical instrument. The control system may temporarily disable the master-slave coupling the enable
(Continued)

said manual reconfiguration, and after the manual reconfiguration, resume the master-slave coupling from the second pose.

12 Claims, 10 Drawing Sheets

(51) Int. Cl.
   *A61B 34/20* (2016.01)
   *A61B 34/30* (2016.01)
   *A61B 90/00* (2016.01)
(52) U.S. Cl.
   CPC ............... *A61B 2034/2059* (2016.02); *A61B 2034/305* (2016.02); *A61B 2034/742* (2016.02); *A61B 2090/065* (2016.02)

(56) References Cited

U.S. PATENT DOCUMENTS

| | | | |
|---|---|---|---|
| 2020/0038126 A1 | 2/2020 | Cau | |
| 2020/0121403 A1 | 4/2020 | Awano et al. | |

FOREIGN PATENT DOCUMENTS

| | | | |
|---|---|---|---|
| WO | 2015142784 A1 | 9/2015 | |
| WO | 2016054256 A1 | 4/2016 | |

* cited by examiner

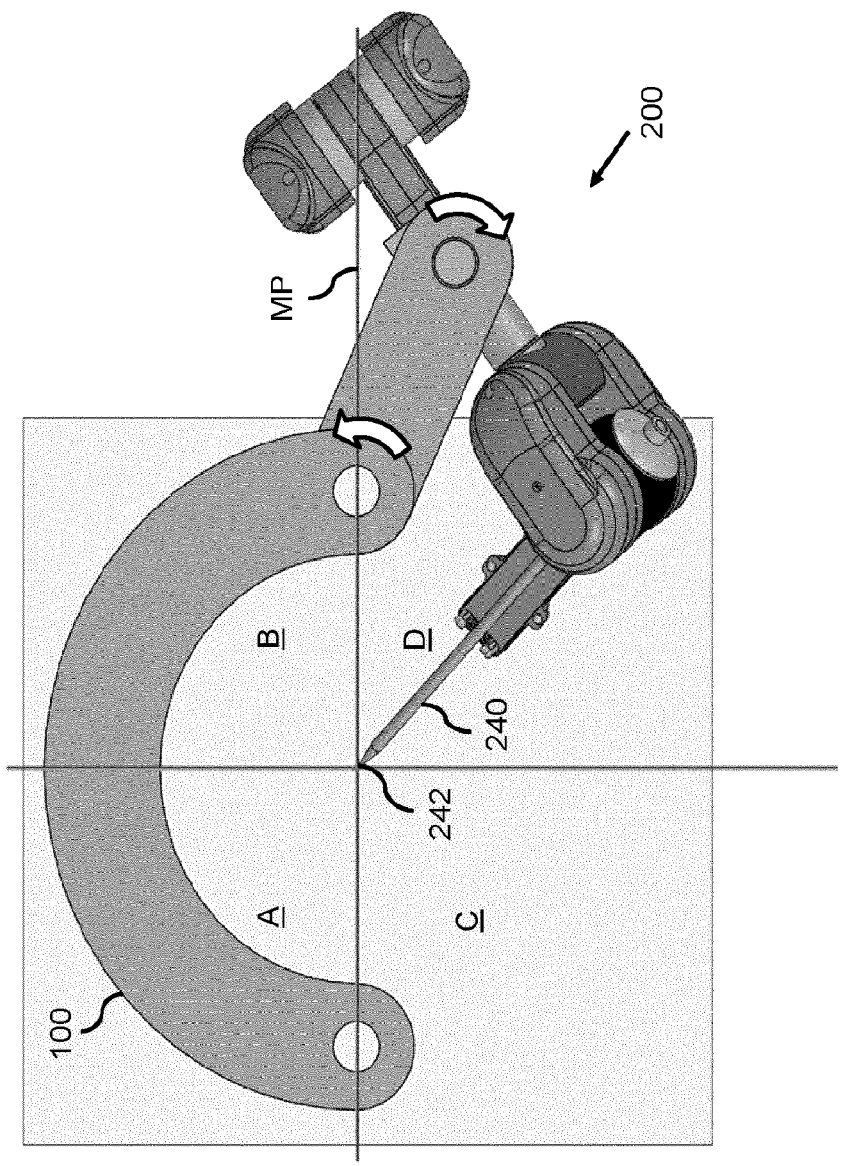

SURGICAL ROBOTIC SYSTEM WITH ADJUSTABLE ANGLE OF APPROACH

CROSS REFERENCE TO RELATED APPLICATIONS

The present application is a U.S. National Phase of International Application No. PCT/EP2021/058213 entitled "SURGICAL ROBOTIC SYSTEM WITH ADJUSTABLE ANGLE OF APPROACH," and filed on Mar. 29, 2021. International Application No. PCT/EP2021/058213 claims priority to European Patent Application No. 20172047.1 filed on Apr. 29, 2020. The entire contents of each of the above-listed applications are hereby incorporated by reference for all purposes.

TECHNICAL FIELD

Embodiments of subject matter disclosed herein relate to a surgical robotic system including a suspension structure, a manipulator arm which is mounted to the suspension structure, and one or more actuators configured to adjust a pose of the manipulator arm to reposition a surgical instrument held by the manipulator arm within a surgical workspace.

BACKGROUND

Nowadays, many surgeries are performed by means of surgical robots. These surgical robots may comprise so-called manipulator arms which generally have an end effector which handles a surgical tool acting upon the patient. Such a manipulator arm may be mounted to a suspension structure so as to allow the manipulator arm to be positioned above and near the surgical target.

Known surgical robotic systems often require extensive pre-operative planning to define the optimal positioning of the manipulator arm with respect to the patient and to define the angle of approach of the surgical instrument(s) with respect to the surgical target. Once the position and angle of approach is defined, these known surgical robotic systems are not designed or intended to be repositioned during surgery. This is typically not a problem for types of surgery that involve larger structures, of which the location and orientation in the patient's body is well-known in advance. Indeed, known surgical robotic systems commonly deal with surgeries where this is the case, such as in gastro-intestinal, eye, brain, or bone surgeries.

However, in microsurgical procedures, a common task is to reconnect small (superficial) blood vessels or nerves. These can be located anywhere on the patient's body. The nature of these small vessels or nerves is that their orientation is not known before the surgery, and may vary drastically, for example from a vertical plane orientation to a horizontal plane orientation. The optimal angle of approach of the surgical instrument is typically defined by the orientation of the vessel. This means that the surgeon has to be ready and flexible in his/her ability to approach the vessels or nerves from drastically different angles, while the surgery is already in progress.

US2020038126 describes a surgical robotic system in the form of a ring-shaped suspension structure on which a carriage is mounted and a manipulator arm which is dockable to the carriage. Together, the carriage and the manipulator arm form a manipulator unit. The manipulator unit may, in case the surgical robotic system is a master-slave robotic system, be a slave unit of the master-slave robotic system. The carriage may move along the ring-shaped suspension structure, which may allow the manipulator arm to approach the surgical target from different angles.

However, US2020038126 necessarily relies on a movable carriage to be able to approach the surgical target from different angles.

SUMMARY OF THE INVENTION

An object of the invention is to obtain a surgical robotic system, which allows a surgical target, such as a microsurgical target, to be approached by the surgical instrument from different angles, without necessarily relying on a movable carriage.

A first aspect of the invention provides a surgical robotic system, including:
- a suspension structure;
- a manipulator arm which is mounted to the suspension structure, wherein the manipulator arm comprises an end effector, wherein the end effector is configured to receive a surgical instrument;
- one or more actuators configured to adjust a pose of the manipulator arm to reposition the surgical instrument within a surgical workspace;
- a control system configured to establish a master-slave coupling between a user input device as a master device and the manipulator arm as a slave device by, on a continuous or periodic basis:
  - receive positioning data from one or more sensors, wherein the positioning data is indicative of the pose of the manipulator arm in the surgical workspace;
  - receive user input data from the user input device, wherein the user input data is indicative of a desired position or change in position of a tip of the surgical instrument in the surgical workspace;
  - based on the positioning data and the user input data, control the one or more actuators to adjust the pose of the manipulator arm to reposition the tip of the surgical instrument;

wherein:
- the manipulator arm is manually reconfigurable from a first configuration in which the manipulator arm assumes a first pose to a second configuration in which the manipulator arm assumes a second pose which is mirrored with respect to the first pose about a mirroring plane which runs through a tip of the surgical instrument;
- the control system is configured to:
  - temporarily disable the master-slave coupling between the user input device and the manipulator arm to enable a manual reconfiguration of the manipulator arm from the first configuration into the second configuration; and
  - after the manual reconfiguration, resume the master-slave coupling between the user input device and the manipulator arm from the second pose.

The above measures provide a so-called master-slave robotic system in which a user may operate a user input device, such as a "joystick" or similar type of device, and in which a manipulator arm may be controlled by a control system such that a tip of a surgical instrument held by the manipulator arm is repositioned in accordance with the user input commands provided by the user input device. Effectively, the control system may establish a master-slave coupling between the user input device as master device and the manipulator arm as slave device. In many cases, the user input device may be physically manipulated to enable the user to provide the user input commands. The control system may thus control the manipulator arm such that a movement of the user input device causes a corresponding movement of the tip of the surgical instrument. For that purpose, the manipulator arm may be actuated using one or more actuators, with such actuators typically being part of the manipulator arm or at least being placed in vicinity of the manipulator arm. For example, if the manipulator arm comprises a series of links connected by respective joints, the actuators may cause rotation about the respective joints, with such rotations resulting in the pose of the manipulator arm in the surgical workspace being adjusted.

The master-slave coupling may be established by the control system on the basis of receiving positioning data from one or more sensors which capture the geometric configuration of the manipulator arm, and thereby the pose of the manipulator arm in the surgical workspace. The geometric configuration of the manipulator arm may be defined and obtained in various ways, for example as a combination of the respective joint angles measured by absolute encoders, or by applying so-called pose recognition to video images of the manipulator arm. In addition, the aforementioned user input data may be received from the user input device. Using the positioning data and the user input data, the control system may then control the one or more actuators to adjust the pose of the manipulator arm so as to position the tip of the instrument at the desired position. The functionality described in this in the preceding paragraph may be known per se from the field of robotic surgical systems.

In accordance with the above measures, the manipulator arm may be manually reconfigurable from a first geometric configuration to a second geometric configuration, with both geometric configurations being mirrored with respect to each other about a mirroring plane which runs through the tip of the surgical instrument. Such manual reconfiguration may, for example, involve a user pushing, pulling or in other ways manipulating individual parts of the manipulator arm. In the aforementioned example where the manipulator arm comprises a series of links connected by respective joints, such mirroring may be performed by the user by rotating the links with respect to each other about the joints, for example by grabbing and moving one link while grabbing and holding still another link. After the manual reconfiguration, the tip of the surgical instrument may be positioned at approximately the same position as before the manual reconfiguration, as the mirroring plane runs through the tip of the surgical instrument but may thereby approach the surgical target from another angle.

In accordance with the above measures, the control system may be configured to temporarily disable the master-slave coupling between the user input device and the manipulator arm to enable the manual reconfiguration of the manipulator arm by the user. Thereby, it may be avoided that the control system counteracts the manual reconfiguration e.g., by controlling the one or more actuators to maintain the manipulator arm's current geometric configuration and thus resist the manual reconfiguration. In addition, by temporarily pausing the master-slave coupling, the control system may temporarily disregard any user input commands given via the user input device to control the position of the tip of the surgical instrument. After the manual reconfiguration, the control system may resume the master-slave coupling between user input device and the manipulator arm from the new geometric configuration of the manipulator arm. Such resumption may be nearly immediate and may not require a renewed calibration of the master-slave coupling since the control system may continue to receive positional data during the manual reconfiguration and may thus know the new pose of the manipulator arm, which includes knowing the new orientation (angle of approach) of the surgical instrument relative to the surgical target.

The above measures may allow a user to easily choose another angle of approach of the surgical instrument to the surgical target without having to rely on a carriage or similar mechanism. Rather, the user may simply mirror the geometric configuration of the manipulator arm and thereafter resume controlling the manipulator arm. In particular, while the angle of approach may in many cases also be changed within a given range using the user input commands, such mirroring may make an entirely different range of angle of approaches possible. This may otherwise not always be possible since the user input device may be primarily directed at positioning the tip of the surgical instrument and actuating the surgical instrument, and may not allow, or not in an intuitive way allow, the pose of the surgical instrument to be significantly changed so as to make an entirely different range of angle of approaches possible.

Nevertheless, in some examples, when the master-slave coupling is resumed from the second pose, the user may experience a continuity in the control of the surgical instrument. Namely, while the geometric configuration of the manipulator arm may be drastically different due to the mirroring, the user may not experience a drastic change in control behavior of the tip of the instrument before and after the reconfiguration. In other examples, there may be a drastic change in control behavior, but this change may be intuitive, for example, by intuitively following from the change in angle of approach of the surgical instrument towards the surgical target.

The surgical robotic system may thereby be well-suited for microsurgical procedures, in which a common task is to reconnect small (superficial) blood vessels or nerves. Namely, the manipulator arm may be manually reconfigured during surgery, which allows the surgeon to be flexible to approach the vessels or nerves from drastically different angles while the surgery is in progress.

The use of a carriage, as in US2020038126, may effectively add a degree of freedom to the surgical robotic system which may be at least partly redundant with the degrees of freedom of the manipulator arm. For example, in case the manipulator arm has six degrees of freedom, the carriage may add a seventh degree of freedom, which may be at least partly redundant in that the manipulator arm may in principle assume a mirrored position enabling the desired flexibility in angle of approach. Such a redundant degree of freedom may cause the surgical instrument to be problematic to control as it may under-constrain the position and orientation of the instrument tip. The invention may provide flexibility in terms of angle of approach with the already available degrees of freedom by the control system being configured to temporarily decouple the master-slave coupling during the manual reconfiguration of the manipulator arm into a mirrored configuration. This functionality may render the use of a carriage unnecessary. In addition, the carriage may typically comprise one or more sensors, actuators, and bearings or guiding rails, which may otherwise increase the cost and complexity of the surgical robotic system.

Optionally, the manipulator arm comprises a series of links connected by respective joints, and the positioning data is indicative of joint angles of the respective joints. The manipulator arm may thus be a serial robot arm, or comprise a serial robot arm part, which may for example have three degrees of freedom, but preferably at least five degrees of freedom. It will be appreciated, however, that other types of manipulator arms are equally conceivable, such as parallel robot arms and master-slave systems based on magnetic field propulsion or actuation.

Optionally, the positioning data is received from one or more absolute encoders which measure the respective joint angles.

Optionally, the control system is configured to, when the master-slave coupling is enabled:
  use a forward kinematics model to determine the pose of the manipulator arm at which the tip of the instrument assumes the desired position or change in position,
  use an inverse kinematics model to determine the joint angles at which the manipulator arm assumes the pose, and
  control the one or more actuators to cause the joints of the manipulator arm to assume said determined joint angles.

Such use of a forward kinematics model and an inverse kinematics model is known per se, and allows user input commands which pertain to a position of the tip of the surgical instrument to be translated into a required pose of the manipulator arm and in turn into corresponding joint angles of the joints of the manipulator arm.

Optionally, the control system is configured to, after the manual reconfiguration of the manipulator arm and before resuming the master-slave coupling:
  reconstruct the second pose of the manipulator arm from the positioning data, and
  adjust the inverse kinematics model to account for the manipulator arm assuming the second pose.

The inverse kinematics model typically includes the real-time coordinates of the manipulator arm, with the term "real-time coordinates" here referring to geometric coordinates which define a current pose of the manipulator arm. Before resuming the master-slave coupling, the inverse kinematics model may thus be updated by the control system to reflect the new coordinates of the manipulator arm. Such coordinates may be obtained in the form of the aforementioned positioning data, which may be received after, but also during, the manual reconfiguration of the manipulator arm.

Optionally, the inverse kinematics model includes a first transformation matrix for the manipulator arm and a second transformation for the user input device, and wherein the control system is configured to, after the manual reconfiguration of the manipulator arm and before resuming the master-slave coupling:
  adjust the inverse kinematics model by adapting the first transformation matrix to account for the manipulator arm assuming the second pose.

Optionally, the user is enabled to affect the disabling and/or the resuming of the master-slave coupling via the user input device or via a further user input device. This may avoid the need for the system to automatically detect a manual reconfiguration, but may rather allow a user to indicate when the master-slave coupling is to be paused and/or resumed, e.g., by appropriately operating the user input device or a further user input device which is separate from the (first) user input device.

For example, the user input device may be a joystick, while the further user input device may include one or more foot-pedals. Such use of different input modalities may prevent the user from accidentally disabling the master-slave coupling, for example when moving the manipulator arm using the joystick. It will be appreciated, however, that these types of user input devices may be examples and that other types of user input devices may be used as well, for example representing different user input modalities. Both user input devices may be of a same or of a different modality.

Optionally, the control system is configured to:
  disable the master-slave coupling upon detecting a press-and-hold of the one or more foot-pedals, and
  resume the master-slave coupling upon detecting a release of the one or more foot-pedals.

Optionally, when the master-slave coupling is disabled, the control system is configured to:
  Control the one or more actuators to move the manipulator arm into a new position and/or orientation in accordance with the external force if an external force above a predefined threshold is applied to the manipulator arm, and
  control the one or more actuators to maintain the new position and/or orientation if the external force falls below the predefined threshold.

Optionally, if the external force above the predefined threshold is applied to the manipulator arm, the control system is configured to control the one or more actuators to keep the tip of the instrument at substantially a same position while moving the manipulator arm.

Optionally, the manipulator arm has a pivot axis at or near a mounting point at which the manipulator arm is mounted to the suspension structure, the manual reconfiguration of the manipulator arm comprises pivoting the manipulator arm about the pivot axis, and the mirroring plane runs through the tip of the surgical instrument and the pivot axis.

Optionally, the suspension structure is a circular or semi-circular structure to be centered above and around a surgical target, wherein the suspension structure comprises different mounting points for mounting the manipulator arm, and wherein manipulator arm is mounted to the suspension structure at one of the mounting points.

Optionally, the surgical robotic system comprises two manipulator arms which are mounted to the suspension structure at two different mounting points, wherein the two different mounting points are substantially opposite to each other along the circular or semi-circular structure.

Optionally, the mirroring plane of each of the manipulator arms runs through both mounting points.

It will be appreciated by those skilled in the art that two or more of the above-mentioned embodiments, implementations, aspects and/or optional aspects of the invention may be combined in any way deemed useful.

BRIEF DESCRIPTION OF THE FIGURES

These and other aspects of the invention are apparent from and will be elucidated with reference to the embodiments described hereinafter. In the drawings.

FIGS. 2A-2D each show a top-down view of the suspension structure and the manipulator arm, and together illustrate how the manipulator arm may be manually reconfigured to approach a surgical target from a wide range of angles;

It should be noted that items which have the same reference numbers in different figures, have the same structural features and the same functions, or are the same signals. Where the function and/or structure of such an item has been explained, there is no necessity for repeated explanation thereof in the detailed description.

DETAILED DESCRIPTION

The following relates to a surgical robotic system which may include one or multiple manipulator arms which may be suspended above a patient by means of a suspension frame, which may elsewhere also be referred to as "suspension structure". A respective manipulator arm may have an end effector which holds a surgical instrument, which may also be simply referred to as "instrument". The surgical instrument may be removably attached to the end effector, for example to facilitate sterilization or to allow exchange with other (types of) surgical instruments.

Figure 1:
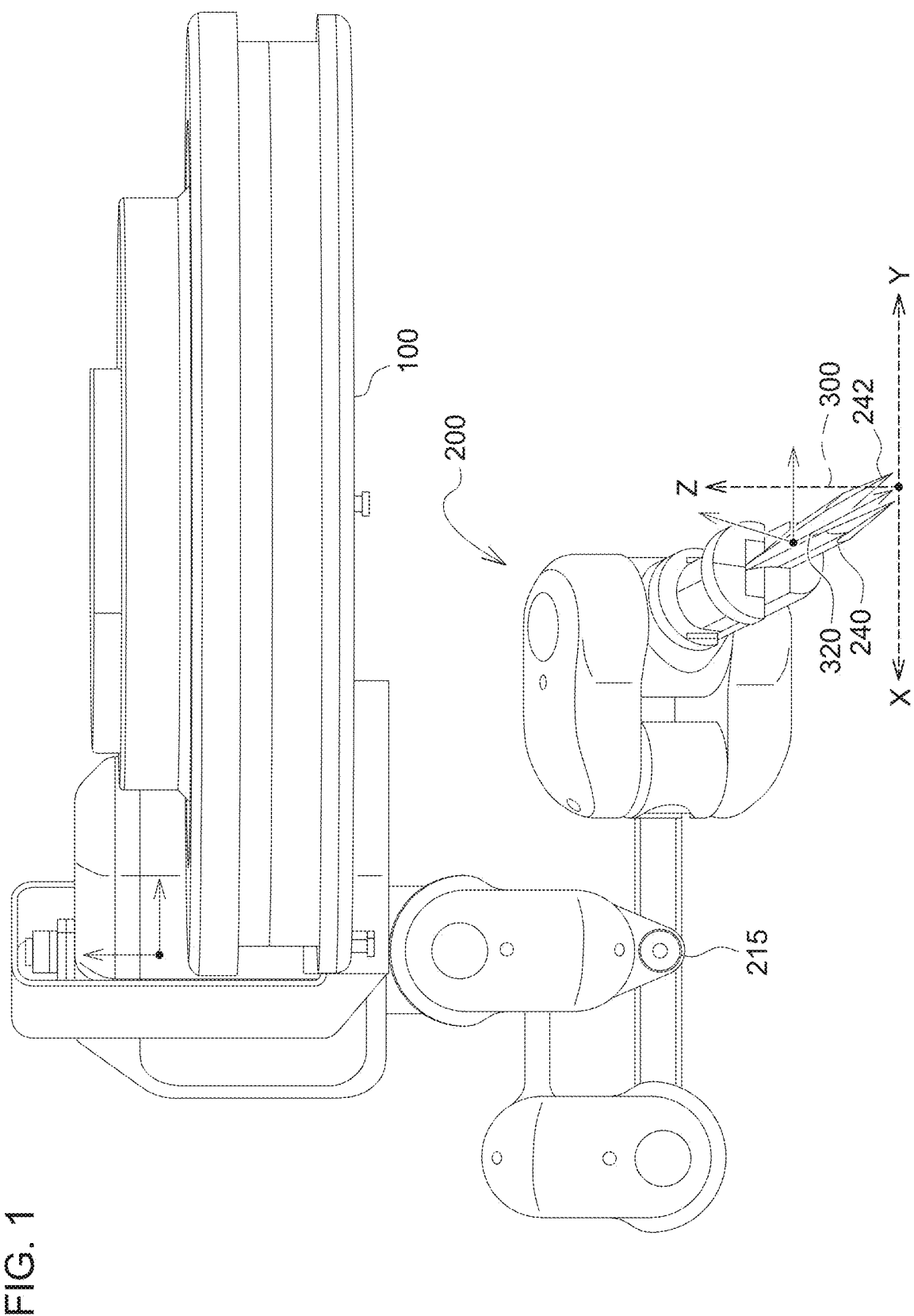
FIG. 1 shows a side-view of a part of a surgical robotic system, showing a suspension structure to which a manipulator arm holding a surgical instrument is mounted, wherein the manipulator arm is manually reconfigurable to be mirrored in pose about a mirroring plane running through a tip of the surgical instrument.

FIG. 1 shows an example of part of such a surgical robotic system, showing the suspension structure 100 and the manipulator arm 200 which includes the end effector and which holds the surgical instrument 240. The surgical instrument 240 is shown to have a tip 242 which may approach a surgical target during surgery. The surgical target may for example be a blood vessel or nerve or other anatomical patient part, and in general may represent a surgical point of interest within an operation site.

Figure 3:
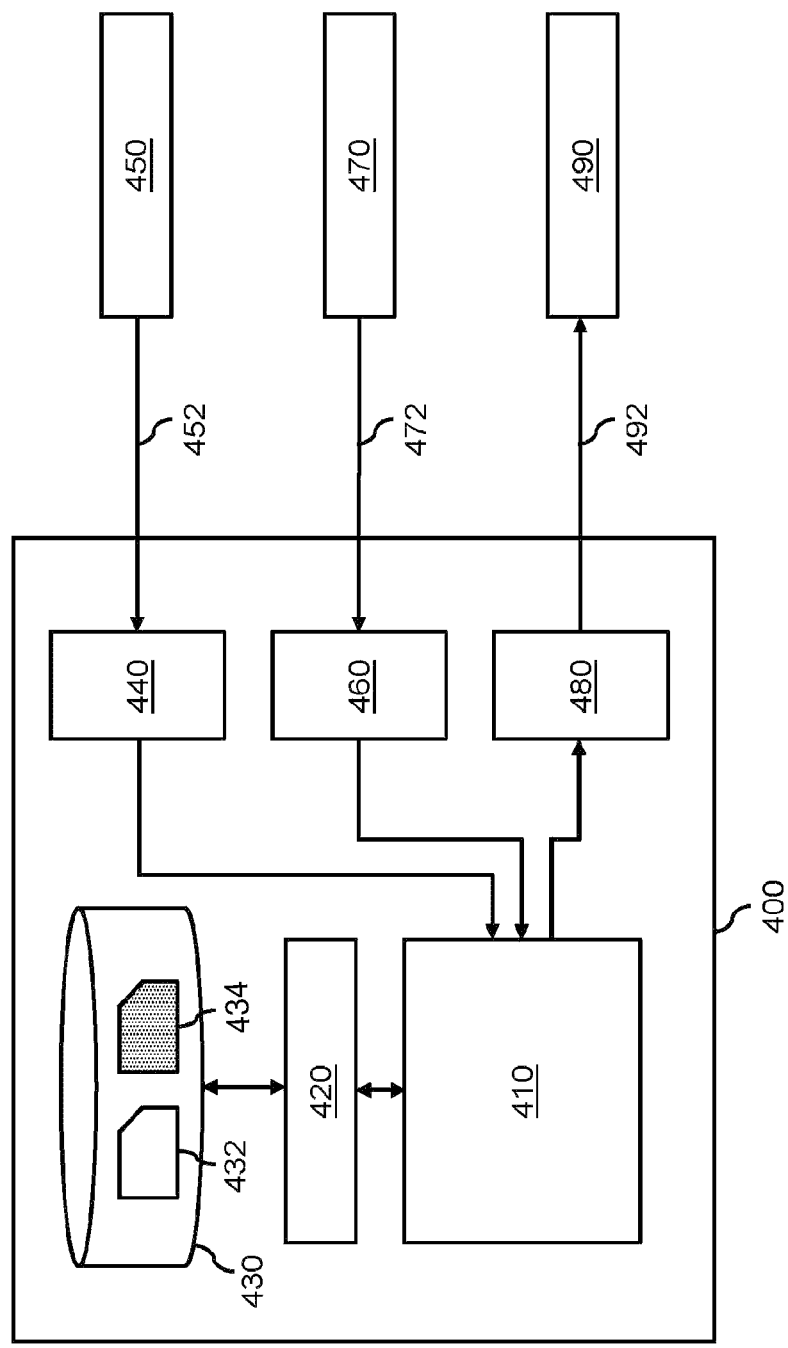
FIG. 3 shows a control system which is configured to temporarily disable a master-slave coupling between a user input device operated by a user and the manipulator arm to enable the manual reconfiguration of the manipulator arm.

Not shown in FIG. 1 are other parts of the surgical robotic system, such as a base structure to which the suspension structure may be mounted, actuator(s) which allow the manipulator arm to be repositioned and reoriented in the surgical workspace, actuator(s) which allow the surgical instrument to be actuated, etc. Such actuators per se may be of a known type, for example electric motors. Also not shown in FIG. 1 is a user input device which may be used to control the manipulator arm 200. Such a user input device per se may be of a known type, such as a joystick. In some examples, there may be multiple user input devices, such as multiple joysticks, or joystick(s) and foot-pedal(s), etc. Also not shown in FIG. 1, but subsequently shown in FIG. 3, is a control system which may translate user input commands provided by the user input device into actuation commands for the actuators of the surgical robotic system.

With continued reference to FIG. 1, the manipulator arm 200 may have a fixed mounting point on the suspension structure 100, from which the manipulator arm 200 may be manually oriented in a first pose, such that the instrument 240 has a first angle of approach with respect to the surgical target. This is also illustrated in FIG. 2A, which shows a top-down view of a part of the surgical robotic system of FIG. 1.

Figure 2A:
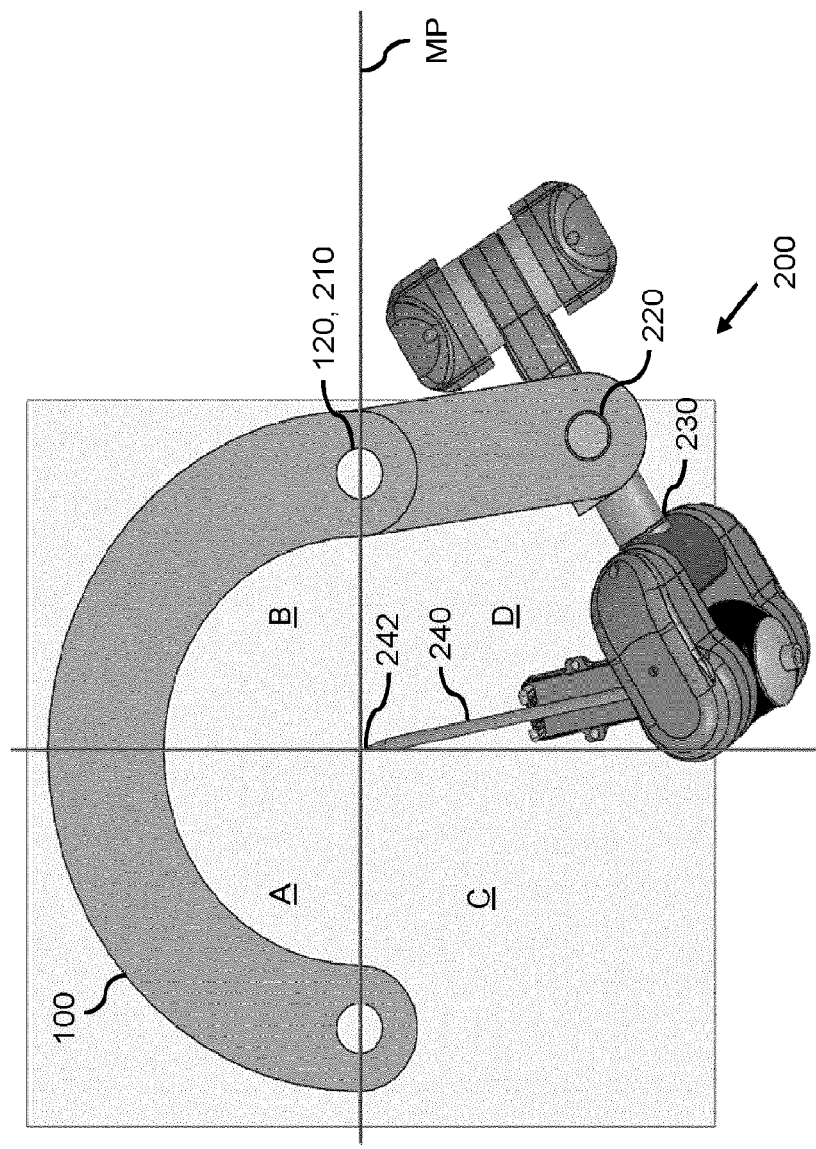

More specifically, FIG. 2A shows that the suspension structure 100 is in this example semicircular shaped, e.g., in the form of a half circle. However, this is not a limitation, in that the suspension structure may also have another shape. Further shown is a fixed mounting point 120 on the suspension structure 100 to which the manipulator arm 200 may be attached. Here, the term "fixed" may refer to the position of the mounting point 120 on the suspension structure 100. The manipulator arm 200 may at the same time be pivotable around the fixed mounting point 120, and thereby pivotable around a (vertical) pivot axis 210. Further shown are other rotation axes 220, 230 of the manipulator arm 200. It is noted that such rotation axes may be provided by respective joints of the manipulator arm 200 around which respective links of the manipulator arm 200 may be rotated. It will be further appreciated that FIG. 2A does not show all possible rotation axes of the manipulator arm 200. However, in general, the manipulator arm 200 may have a sufficiently high degree of (rotational) freedom, for example by having five or six degrees of freedom, for microsurgical procedures. These rotational degrees of freedom may, but do not need to, include the abovementioned pivot axis 210 around the fixed mounting point 120. In examples without pivot axis, the corresponding rotational degree of freedom may be provided by (an)other joint(s).

Figure 2C:
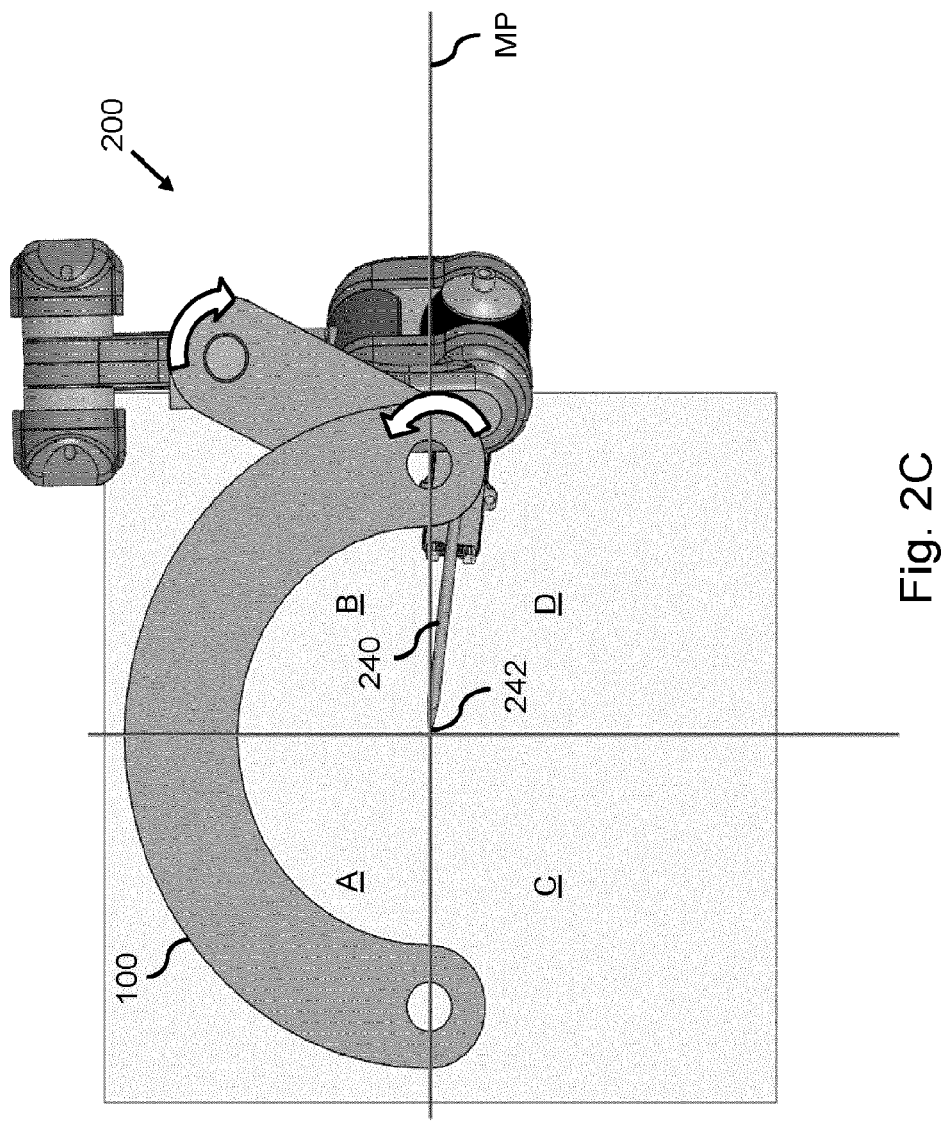

FIGS. 2A-2C jointly illustrate that the rotation axes of the manipulator arm 200, including the pivot axis 210, may allow the surgical instrument 240 to approach the surgical target from various angles. Namely, by rotating parts of the manipulator arm 200 around the various rotation axes, the pose of the manipulator arm 200 may be adjusted, allowing the surgical instrument 240 to approach the surgical target from different angles. The rotations are illustrated in FIGS. 2B-2C and also later in FIG. 2D by curved arrows, which illustrate the respective rotations compared to a preceding figure. However, it will be appreciated that such curved arrows are meant purely for illustration purposes and do not define the exact rotation, e.g., in terms of degrees of rotation.

In the example of FIGS. 2A-2D, but also in following FIGS. 4A-4D, four quadrants A-D are defined with respect to the surgical target, with the surgical target being located at the intersection of the four quadrants A-D but otherwise not explicitly indicated. The quadrants may each represent a part of the accessible surgical workspace but may also define a range of angles from which the surgical target may be approached. This quadrant-visualization may illustrate that the manipulator arm 200 may be manually reconfigured, e.g., by the manual rotation around respective rotation axes as shown in FIGS. 2B and 2C, so that it may approach the surgical target from quadrant D, but that it may also be manually reconfigured such that it reaches the surgical target from an entirely different range of angles, e.g., from another quadrant.

Figure 2D:
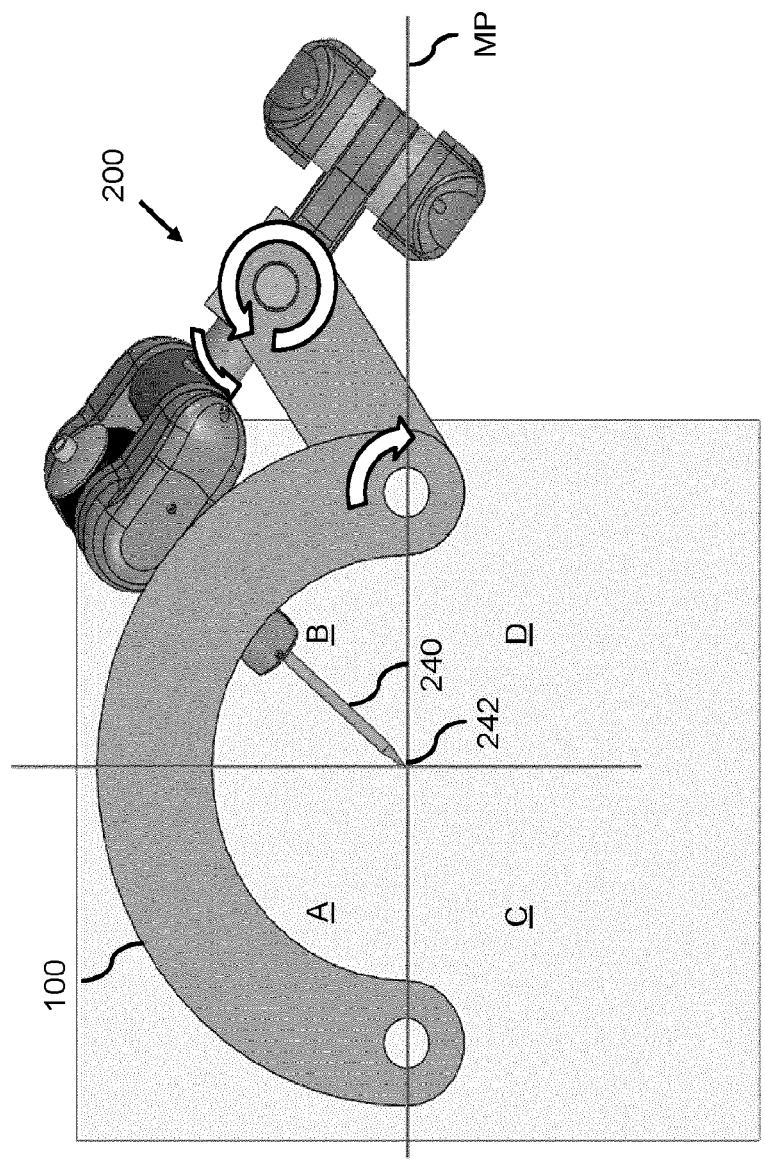

The latter is illustrated in FIG. 2D, where the manipulator arm 200 is shown to be rotated about its various rotation axes that it reaches the surgical target from the angles of approach corresponding to quadrant B. For that purpose, the manipulator arm 200 may be designed to provide sufficient degrees of freedom to allow the manipulator arm 200 to assume a pose which is mirrored from an earlier pose with respect to a mirroring plane which runs through the tip 242 of the surgical instrument. In FIGS. 2A-2D, but also in the following FIGS. 4A-4D, this mirroring plane MP is shown to run through the mounting point 120 of the manipulator arm 200, and thereby through the pivot axis 210 of the manipulator arm 200, and through a center point of the (semi)circular suspension structure 100, and thereby through a surgical target if the suspension structure 100 is centered around the surgical target. It will be appreciated that this also corresponds to the mirroring plane running through the tip 242 of the instrument if the instrument is with its tip positioned at or near the surgical target.

FIGS. 2A-2D thus illustrate that the manipulator arm 200 may, through the ability to assume a mirrored pose, approach the surgical target at a wide range of angles, e.g., from quadrants B and D. In this respect, it is noted that in practice, the range of angles may overlap between mirrored poses, but at the same time may cover different ranges of approach angles. This ability may be obtained by having a sufficient number of degrees of freedom, e.g., at least three and preferably five or six. In the example of FIGS. 2A-2D, the various rotation axes 220, 230 and the (vertical) pivot axis 210 near the fixed mounting point on the suspension structure 100 may allow the manipulator arm 200 to be manually oriented in a second pose, which is mirrored with respect to the first pose, such that the instrument 240 has a second range of angles of approaches with respect to the surgical point of interest within the operation site. It can be further seen in FIGS. 2A-2D that the tip 242 of the instrument may stay at a substantially same place during the manual reconfiguration from FIG. 2A to FIG. 2D.

FIG. 3 schematically shows a control system 400 which may be configured to establish a master-slave coupling between a user input device as a master device and the manipulator arm as a slave device, and thereby allow a user to reposition the tip of the surgical instrument in the surgical workspace. For that purpose, the control system 400 may comprise one or more processors 410, a data storage 430, a data storage interface 420 and several other interfaces 440, 460, and 480. The interfaces of the control system 400 may take any suitable form, such as low-level electrical interfaces, computer buses, serial interfaces, parallel interfaces, network interfaces, etc.

The control system 400 may include a user input device interface 440 which may be configured to receive user input data 452 from one or more user input devices 450. As also explained elsewhere, the user input devices may take various forms, such as one or a combination of joysticks, foot-pedals, buttons, touch-sensitive surfaces, etc.

The control system 400 may further include a sensor interface 460 which may be configured to receive sensor data 472 from one or more sensors 470. The sensor data 472 may represent positioning data, in that it may be indicative of a pose or geometric configuration of the manipulator arm. For example, the one or more sensors 470 may be absolute encoders arranged at respective joints of the manipulator arm, and the control system 400 may receive the sensor data 472 as being indicative of the joint angles of the respective joints. These joint angles may together define or at least be indicative of a pose of the manipulator arm. In other examples, the sensor data 472 may be image data obtained by a video camera directed at the manipulator arm. Such sensor data may be analyzed to determine the pose of the manipulator arm. The resulting analysis data may define or at least be indicative of the pose of the manipulator arm. Various other types of sensors or combinations of sensors may equally be used to detect the pose of the manipulator arm in (pseudo) real-time.

The control system 400 may further include an actuator interface 480 through which the control system 400 may control one or more actuators 490 of the manipulator arm, or of the surgical robotic system in general. For that purpose, the control system 400 may generate actuator control data 492. Such actuators 490 may take any suitable form, including but not limited to (piezo)electric, hydraulic, pneumatic, magnetic and/or mechanical actuators. Specific yet non-limiting examples include electrical motors, electroactive polymers, hydraulic cylinders, piezoelectric actuators, pneumatic actuators, servomechanisms, solenoids, stepper motors, etc. In some examples, the control system 400 may, instead or in addition to generating actuator control data 492, control the actuator(s) 490 by selectively providing electrical power.

In general, the control system 400 may be configured to, on a continuous or (semi-) periodic basis, receive user input data 452 from the user input device(s) 450, wherein the user input data is indicative of a desired position or change in position of a tip of the surgical instrument in the surgical workspace, receive the positioning data 472 from the sensor(s) 470, and based on the positioning data 472 and the user input data 452, control the one or more actuators 490, e.g., via the actuator control data 492, to adjust the pose of the manipulator arm to reposition the tip of the surgical instrument.

The control system 400 may be further configured to temporarily disable the master-slave coupling between the user input device and the manipulator arm to enable a manual reconfiguration of the manipulator arm from a current configuration (pose) to a new configuration (pose). For example, the control system 400 may temporarily disable the master-slave coupling at the request of the user, for example on the basis of a specific user input command received from the user input device(s) 450. It will be appreciated that the control system 400 may also register the manual reconfiguration in other ways, e.g., by detecting an external force which is applied to the manipulator arm. After manual reconfiguration, the control system 400 may resume the master-slave coupling between the user input device(s) 450 and the manipulator arm from the new pose. This may involve forward and inverse kinematics models.

Namely, the control system 400 may be configured to, when the master-slave coupling is enabled, use a forward kinematics model to determine the pose of the manipulator arm at which the tip of the instrument assumes the desired position or change in position, and use an inverse kinematics model to determine the joint angles at which the manipulator arm assumes the pose. The control system 400 may be further configured to control the one or more actuators 490 to cause the joints of the manipulator arm to assume said determined joint angles. Both models may be stored and retrieved by the control system 400 from the data storage 430 and via the data storage interface 420. For example, the data storage 430 may store forward kinematics model data 432 representing the forward kinematics model and inverse kinematics model data 434 representing the inverse kinematics model. Such data may represent a structured and therefore machine-readable form of the respective models.

To resume the master-slave coupling between the manipulator arm and the joystick, the control system 400 may be configured to, after the manual reconfiguration of the manipulator arm and before resuming the master-slave coupling, reconstruct the second pose of the manipulator arm from the positioning data, and adjust the inverse kinematics model to account for the manipulator arm assuming the second pose. This may involve providing, as part of inverse kinematics model, a first transformation matrix for the manipulator arm and a second transformation for the user input device, and recalibrating the master-slave coupling by specifically adapting the first transformation matrix to account for the manipulator arm assuming the second pose. It will be appreciated, however, that such calibration may also be performed in other control paradigms, e.g., without specifically using a first and second transformation matrix. In general, by being based on kinematic models which couple the joystick(s) with the manipulator arm, the master-slave coupling may represent a "kinematic" coupling, which may be resumed by the control system 400 after the manual reconfiguration while accounting in this coupling for the change in pose of the manipulator arm.

With continued reference to FIG. 3, the control system 400 may be configured to normally control the one or more actuators 490 to maintain the pose of the manipulator arm when the master-slave coupling between user input device(s) 450 and manipulator arm is enabled and no user input commands to the contrary are received. This may for example involve controlling the actuator(s) 490 to counteract a gravitational force, or in some examples any other external force, such as that of a user attempting to manually reconfigure the manipulator arm. Effectively, when the master-slave coupling is enabled, the manipulator arm may resist manual reconfiguration. Disabling the master-slave coupling may "unlock" the manipulator arm, and thereby for example the pivot axis, to enable manual reconfiguration of the manipulator arm.

The control system 400 may also assist the user in the manual reconfiguration. For example, when the master-slave coupling is disabled, and when an external force above a predefined threshold is applied to the manipulator arm, the control system 400 may control the actuator(s) 490 to move the manipulator arm into a new position and/or orientation in accordance with the external force, and if the external force falls below the predefined threshold, control the actuator(s) 490 to maintain the new position and/or orientation. In addition, or alternatively, the control system 400 may be configured to, if the external force above the predefined threshold is applied to the manipulator arm, control the one or more actuators to keep the tip of the instrument at substantially a same position while moving the manipulator arm.

With continued reference to FIG. 3, the user may be enabled to affect the disabling and/or the resuming of the master-slave coupling via the user input device(s) 450. For example, the control system 400 may be configured to disable the master-slave coupling upon detecting a press-and-hold of one or more foot-pedals, and to resume the master-slave coupling upon detecting a release of the one or more foot-pedals. In a specific example, the control system 400 may implement a state-machine to switch between various software states. Switching between states may be done by a user action, for example the aforementioned pressing-and-holding of two foot-pedals simultaneously. The following provides a specific example of such states:
1. System is in Operational Mode The operational mode may be a standard operating mode of the system, in which the position of the slave manipulator(s) may be controlled by the input received from the joystick(s). Sensor measurements from the joystick(s) may be, via forward kinematics, translated into a reference pose. The reference pose may then be translated into the desired joint angles at the slave manipulator via inverse kinematics. The forward and inverse kinematics may be coupled, such that a position change in either causes a proportional position change in the other. This operational mode may correspond to the master-slave or kinematic coupling as described elsewhere.
2. User Presses and Holds Both Foot-Pedals Simultaneously.

This may cause the state machine to switch from operational mode to manual reposition mode.
3. System is in Manual Reposition Mode In manual reposition mode, the coupling between the forward and inverse kinematics may be purposefully disabled. The sensor measurements of the slave manipulator and the joystick(s) may still be obtained by measurement, but with the control system not acting upon the sensor measurements. As such, if the joystick moves, the slave manipulator may not follow the movement but instead may maintain its current position. If an external force above a defined threshold is applied to the slave manipulator, the slave manipulator may move accordingly until the external force is below said threshold, at which time the manipulator may again maintain its new position. This may be valid for all degrees of freedom in the slave manipulator.

In another example, only selected degrees of freedom may be manually repositioned, whereas other degrees of freedom may remain locked in operational mode. This way, the position of the end effector of the slave manipulator may be held fixed in a specific location, while the pose of the manipulator may be free to change.
4. User Releases Both Foot-Pedals This may cause the state machine to switch from manual reposition mode back to operational mode.
5. System is Back in Operational Mode With continued reference to FIG. 3, the data storage interface 420 may be a memory interface or a persistent storage interface, e.g., a hard disk or an SSD interface, but also a personal, local, or wide area network interface such as a Bluetooth, Zigbee or Wi-Fi interface or an ethernet or fiberoptic interface. The data storage 430 may be an internal data storage of the control system 400, such as memory or a hard drive or SSD, but also an external, e.g., a network-accessible, data storage.

In general, the control system 400 may be embodied as, or in, a single device or apparatus, such as a workstation or a server, which may be electrically connected with the manipulator arm. The device may also be an embedded device which is embedded in, e.g., a base structure or other part of the robotic surgical system. In general, the device or apparatus may comprise one or more microprocessors which execute appropriate software. For example, the processor(s) 410 of the control system 400 may be embodied by a single Central Processing Unit (CPU), but also by a combination or system of such CPUs and/or other types of processing units. Software implementing functionality of the control system 400 as described in this specification may have been downloaded and/or stored in a corresponding memory, e.g., a volatile memory such as RAM or a non-volatile memory such as Flash. Alternatively, the processor(s) 410 of the control system 400 may be implemented in the device or apparatus in the form of programmable logic, e.g., as a Field-Programmable Gate Array (FPGA). In general, each functional unit of the control system 400 may be implemented in the form of a circuit. The control system 400 may also be implemented in a distributed manner, e.g., involving different devices or apparatuses, such as distributed local or cloud-based servers or as a client and server.

Each method, algorithm, or pseudo-code described in this specification may be implemented on a computer as a computer-implemented method, as dedicated hardware, or as a combination of both. Instructions for the computer, e.g., executable code, may be stored on a computer-readable medium, e.g., in the form of a series of machine-readable physical marks and/or as a series of elements having different electrical, e.g., magnetic, or optical properties or values. The executable code may be stored in a transitory or non-transitory manner. Examples of computer-readable mediums include memory devices, optical storage devices, integrated circuits, etc.

Figure 4A:
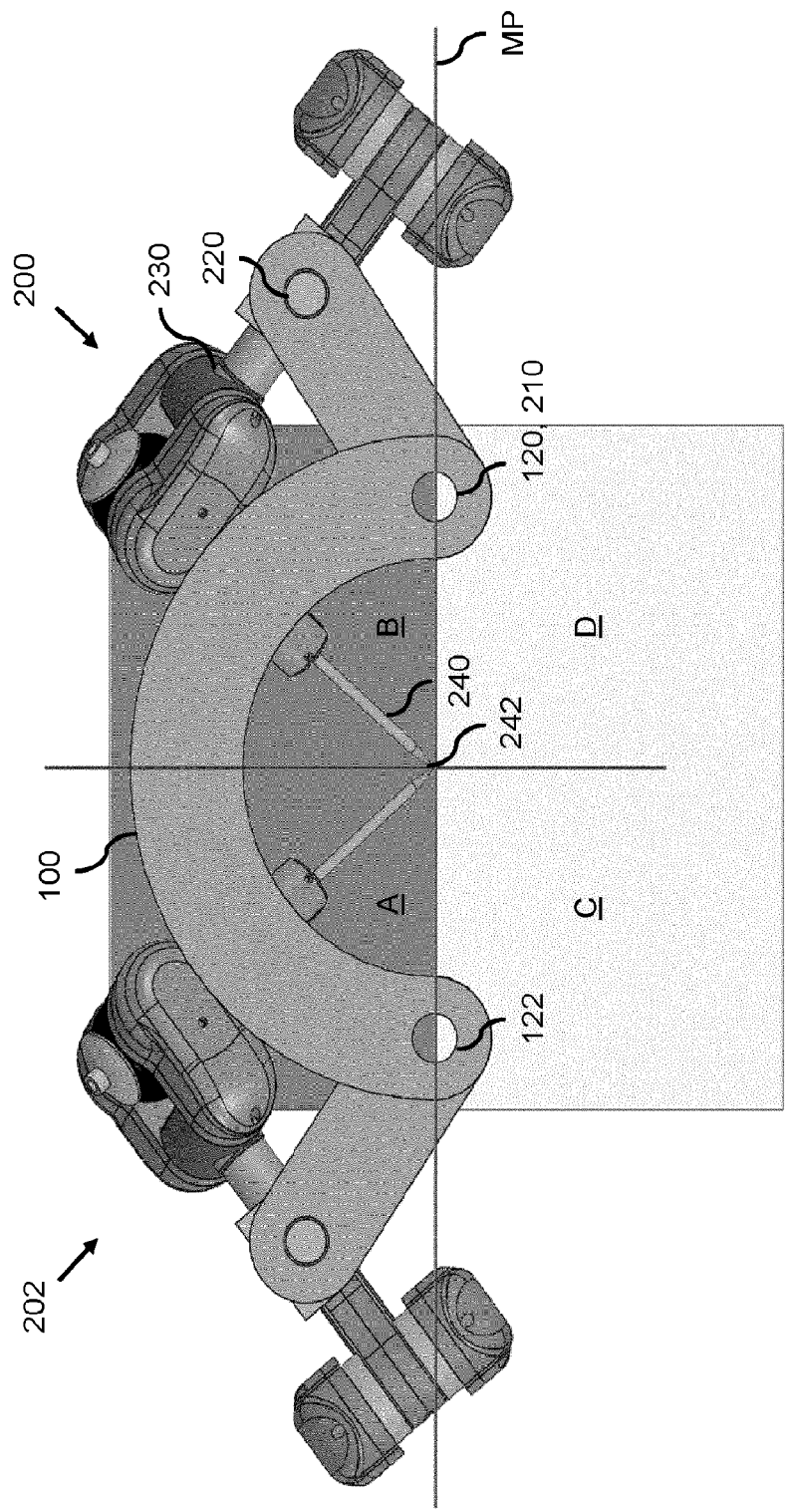
FIGS. 4A-4D each show a top-down view of the suspension structure to which two manipulator arms are mounted, with the respective figures illustrating that two manipulator arms may approach a surgical target from all angles.
Figure 4B:
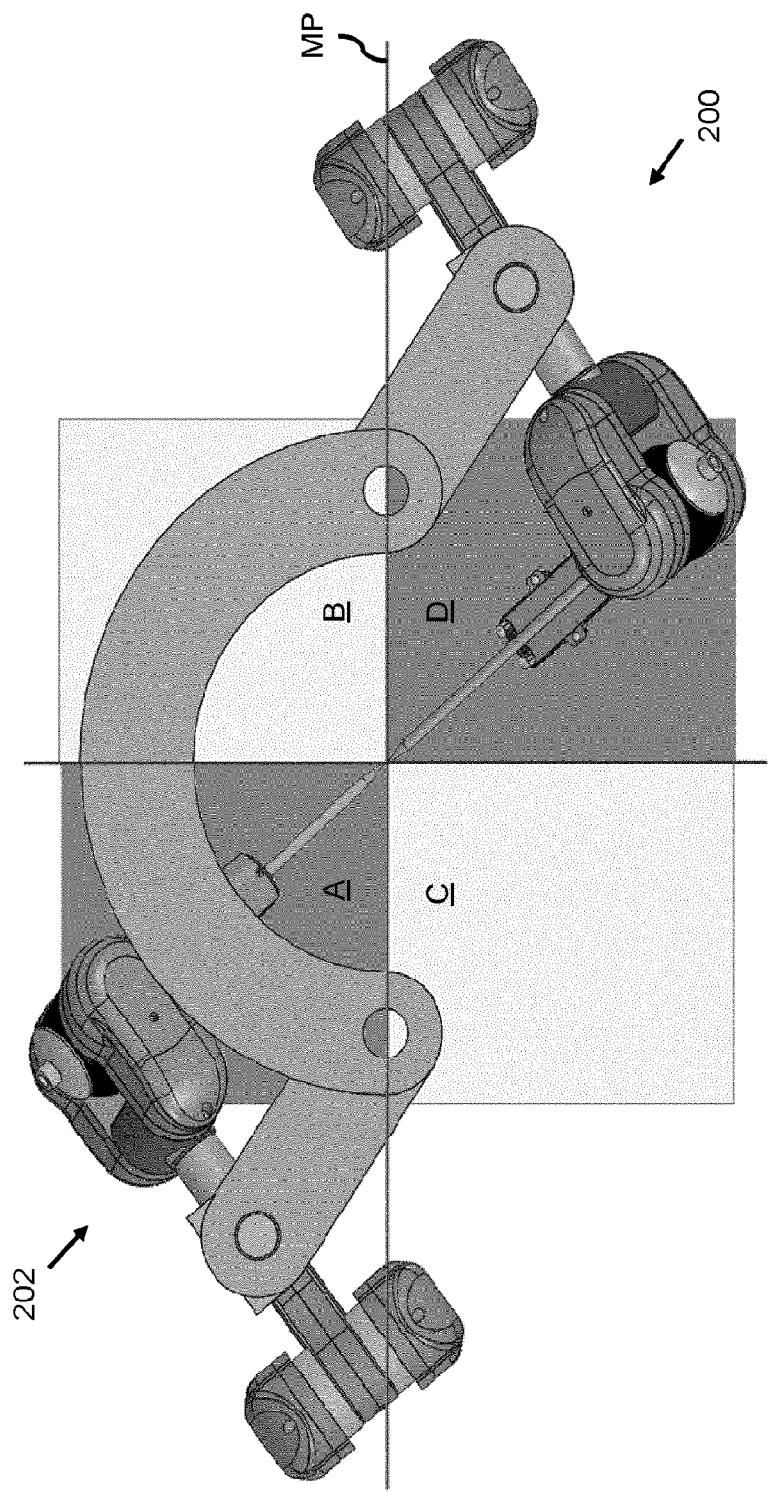
Figure 4C:
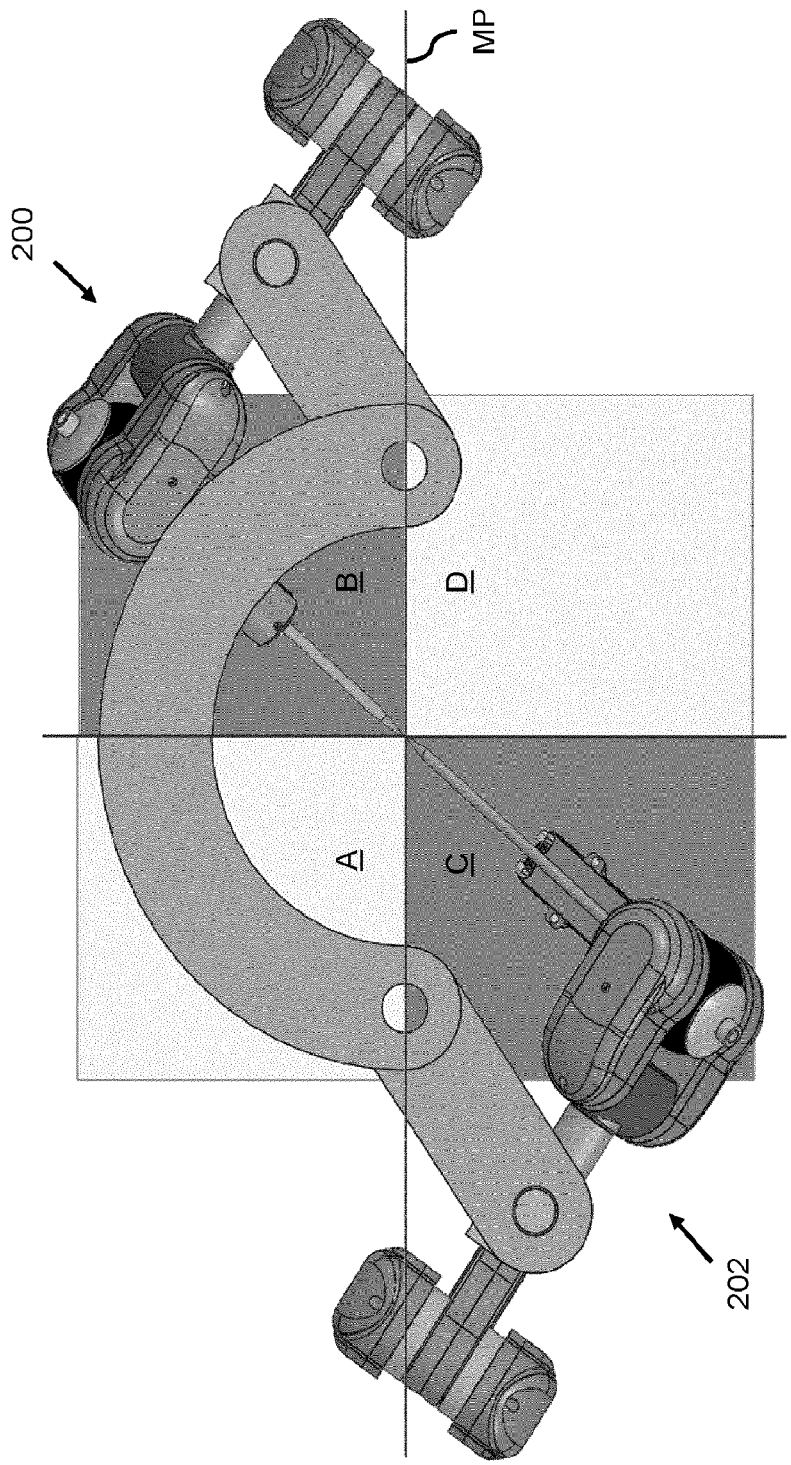
Figure 4D:
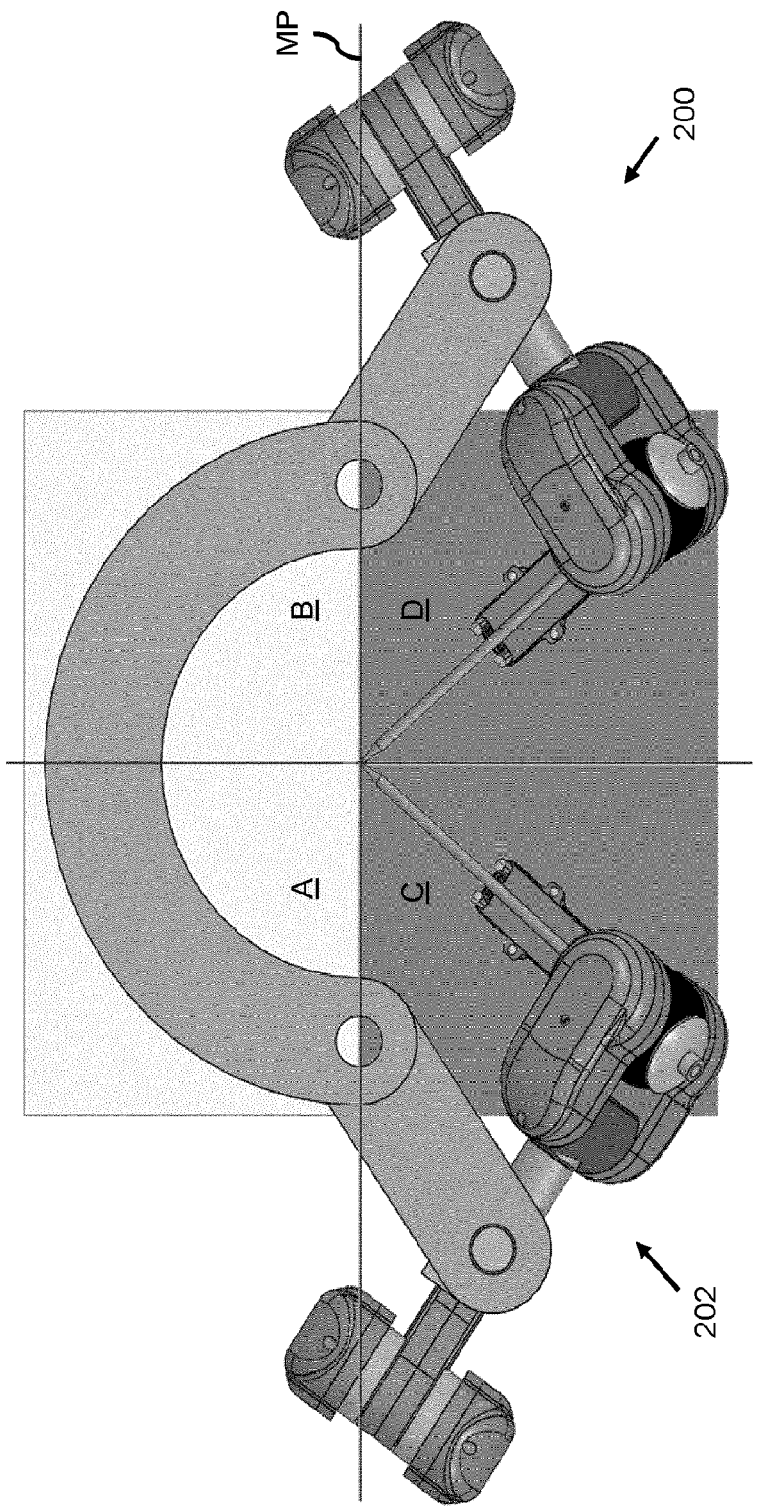

FIGS. 4A-4D each show a top-down view of the suspension structure 100 to which two manipulator arms 200, 202 are mounted at respective (fixed) mounting points 120, 122 on the suspension structure 100, with the respective figures illustrating that two manipulator arms may approach a surgical target from all angles. Namely, if an approach from quadrants A and B is referred to as an approach from a "distal side" and an approach from quadrants C and D as an approach from a "proximal" side, for example because an operator may be sitting at this side, then FIG. 4A shows the left and right instruments approaching the surgical target from the distal side, FIG. 4B shows the left instrument approaching the surgical target from the distal side and the right instrument approaching from the proximal side, FIG. 4C shows the left instrument approaching the surgical target from the proximal side and right instrument approaching from the distal side, and FIG. 4D shows the left and right instruments both approaching the surgical target from the proximal side. This way, the surgical target may be approached from all angles, enabling the robotic surgical system to accommodate for the orientation of a blood vessel or nerve only becoming known during (start of) the surgical procedure. In this respect, it is noted that an operator may also be sitting elsewhere, including a remote location, and thus that the terms "proximal side" and "distal side" are mere exemplary labels used to distinguish the sides.

In general, if more than one manipulator arm is used, the angle of approach of the instrument(s) held by one manipulator arm may be repositioned independently of the others by each manipulator arm being independently reconfigurable in pose.

With continued reference to FIG. 1, the surgical robotic system may be controlled based on a global (and absolute) reference frame 300 and within this global reference frame one or more local (and relative) reference frames 310 of which the position and orientation with respect to the global reference frame 300 may be fixed and known to the control system. This may allow the conversion of a relative movement of an instrument tip within its local reference frame 320 (also referred to as instrument reference frame 320) to an absolute movement within the global reference frame 300. This in turn may for example allow other instrument tips (e.g., of both manipulator arms 200, 202 as described with reference to FIGS. 4A-4D) to follow the movement but translated to their own local reference frame. The position of the instrument's tip in the instrument reference frame 320 may be measured with respect to the local reference frame 310, which measurements may be obtained as the aforementioned positional data. This measurement may be either absolute or relative (e.g., measuring only a change with respect to a previous value). Because the position of the local reference frame 310 within the global reference frame 300 may be known, and therefore also the position of the instrument tip 242 within the global frame reference 300, a coupling may be made between all instrument tips such that the movements of these instrument tips are correlated, e.g., to move in the same direction within the global reference frame.

It should be noted that the above-mentioned embodiments illustrate rather than limit the invention, and that those skilled in the art will be able to design many alternative embodiments without departing from the scope of the disclosure described herein.

Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

LIST OF REFERENCE AND ABBREVIATIONS

The following list of references and abbreviations is provided for facilitating the interpretation of the drawings and shall not be construed as limiting the disclosure described herein.

A-D quadrant
MP mirroring plane
100 suspension structure
120, 122 mounting point
200, 202 manipulator arm
210 rotation axis (pivot axis)
215 rotation axis
220 rotation axis
230 rotation axis
240 surgical instrument
242 surgical instrument tip
300 global reference frame
310 local reference frame
320 local (instrument) reference frame
400 control system
410 processor(s)
420 data storage interface
430 data storage
432 forward kinematics model data
434 inverse kinematics model data
440 user input device interface
450 user input device(s)
452 user input data
460 sensor interface
470 sensor(s)
472 sensor data (positioning data)
480 actuator interface
490 actuator(s)
492 actuator control data

The invention claimed is:

1. A surgical robotic system, comprising:
a suspension structure;
two manipulator arms mounted to the suspension structure, wherein each manipulator arm of the two manipulator arms comprises an end effector, wherein the end effector is configured to receive a surgical instrument, wherein the suspension structure is a circular or semi-circular structure to be centered above and around a surgical target, wherein the suspension structure comprises different mounting points for mounting the two manipulator arms, wherein the two manipulator arms are mounted to the suspension structure at two different mounting points, wherein the two different mounting points are substantially opposite to each other along the circular or semi-circular structure, and wherein a mirroring plane of each of the two manipulator arms runs through both mounting points;
one or more actuators configured to adjust a pose of the two manipulator arms to reposition the surgical instrument within a surgical workspace;
a control system configured to establish a master-slave coupling between a user input device as a master device and the two manipulator arms as a slave device by and on a continuous or periodic basis:

receive positioning data from one or more sensors, wherein the positioning data is indicative of the pose of the two manipulator arms in the surgical workspace;

receive user input data from the user input device, wherein the user input data is indicative of a desired position or change in position of a tip of the surgical instrument in the surgical workspace;

based on the positioning data and the user input data, control the one or more actuators to adjust the pose of the two manipulator arms to reposition the tip of the surgical instrument;

wherein:

the two manipulator arms are manually reconfigurable from a first configuration in which at least one of the two manipulator arms assume a first pose to a second configuration in which the at least one of the two manipulator arms assume a second pose which is mirrored with respect to the first pose about the mirroring plane which runs through the tip of the surgical instrument; and wherein the control system is configured to:

temporarily disable the master-slave coupling between the user input device and the two manipulator arms to enable a manual reconfiguration of the at least one of the two manipulator arms from the first configuration into the second configuration; and after the manual reconfiguration, resume the master-slave coupling between the user input device and the at least one of the two manipulator arms from the second pose.

2. The surgical robotic system according to claim 1, wherein each of the two manipulator arms comprises a series of links connected by respective joints, and wherein the positioning data is indicative of joint angles of the respective joints.

3. The surgical robotic system according to claim 2, wherein the positioning data is received from one or more absolute encoders which measure the respective joint angles.

4. The surgical robotic system according to claim 2, wherein, when the master-slave coupling is enabled the control system is configured to:

use a forward kinematics model to determine the pose of the at least one of the two manipulator arms at which the tip of the surgical instrument assumes the desired position or change in position, use an inverse kinematics model to determine the joint angles at which the at least one of the two manipulator arms assumes the pose, and control the one or more actuators to cause the respective joints of the at least one of the two manipulator arms to assume said determined joint angles.

5. The surgical robotic system according to claim 4, wherein after the manual reconfiguration of the at least one of the two manipulator arms and before resuming the master-slave coupling, the control system is configured to:

reconstruct the second pose of the at least one of the two manipulator arms from the positioning data, and adjust the inverse kinematics model to account for the at least one of the two manipulator arms assuming the second pose.

6. The surgical robotic system according to claim 5, wherein the inverse kinematics model comprises a first transformation matrix for the two manipulator arms and a second transformation for the user input device, and wherein after the manual reconfiguration of the at least one of the two manipulator arms and before resuming the master-slave coupling, the control system is configured to:

adjust the inverse kinematics model by adapting the first transformation matrix to account for the manipulator arm assuming the second pose.

7. The surgical robotic system according to claim 5, wherein the user is enabled to affect the disabling and/or the resuming of the master-slave coupling via the user input device or via a further user input device.

8. The surgical robotic system according to claim 7, wherein the user input device is a joystick, and wherein the further user input device comprises one or more foot-pedals.

9. The surgical robotic system according to claim 8, wherein the control system is configured to:

disable the master-slave coupling upon detecting a press-and-hold of the one or more foot-pedals, and resume the master-slave coupling upon detecting a release of the one or more foot-pedals.

10. The surgical robotic system according to claim 1, wherein when the master-slave coupling is disabled the control system is configured to execute instructions, wherein if an external force above a predefined threshold is applied to one of the two manipulator arms, control the one or more actuators to move the one of the two manipulator arms into a new position and/or orientation in accordance with the external force, and if the external force falls below the predefined threshold, control the one or more actuators to maintain the new position and/or orientation.

11. The surgical robotic system according to claim 10, wherein if the external force above the predefined threshold is applied to the one of the two manipulator arms, the control system is configured to control the one or more actuators to keep the tip of the surgical instrument at substantially a same position while moving the one of the two manipulator arms.

12. The surgical robotic system according to claim 1, wherein each of the two manipulator arms has a pivot axis at or near a mounting point at which each of the two manipulator arms is mounted to the suspension structure, wherein the manual reconfiguration of the at least one of the two manipulator arms comprises pivoting the at least one of the two manipulator arms about the pivot axis, and wherein the mirroring plane runs through the tip of the surgical instrument and the pivot axis.

* * * * *